United States Patent [19]

Gargiulo et al.

[11] 4,275,153
[45] Jun. 23, 1981

[54] ANALYTICAL FLUOROGENIC SUBSTRATES FOR PROTEOLYTIC ENZYMES

[75] Inventors: Robert J. Gargiulo; Gary A. Mitchell; Patricia M. Hudson; Sharon P. Pochron; Rolf M. Huseby, all of Miami, Fla.; Robert E. Smith, Livermore, Calif.

[73] Assignee: American Hospital Supply Corporation, Evanston, Ill.

[21] Appl. No.: 930,826

[22] Filed: Aug. 3, 1978

[51] Int. Cl.³ .................. C12Q 1/36; C12Q 1/38; C12Q 1/56; C07G 7/00
[52] U.S. Cl. ................................ 435/13; 435/23; 435/24; 260/112.5 R
[58] Field of Search ............ 435/23, 24, 13, 805, 435/810; 260/112.5 R; 424/2, 7

[56] References Cited

U.S. PATENT DOCUMENTS

| | | | |
|---|---|---|---|
| 3,884,896 | 5/1975 | Blomback et al. | 435/13 |
| 3,886,136 | 5/1975 | Claeson et al. | 435/13 |
| 4,016,042 | 4/1977 | Svendsen | 435/23 |
| 4,028,318 | 6/1977 | Aurell et al. | 435/23 |
| 4,070,245 | 1/1978 | Svendsen | 435/23 |
| 4,137,225 | 1/1979 | Ekenstam et al. | 435/23 |
| 4,155,916 | 5/1979 | Smith et al. | 435/23 |
| 4,167,449 | 9/1979 | Gargiulo et al. | 435/24 |
| 4,169,015 | 9/1979 | Ekenstam et al. | 435/13 |

Primary Examiner—Thomas G. Wiseman

Attorney, Agent, or Firm—Robert E. Hartenberger; Edward A. Figg

[57] ABSTRACT

Fluorogenic substrates for proteolytic enzymes having the formula:

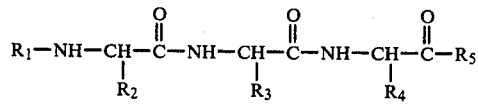

or acid salts thereof wherein:

$R_1$ is hydrogen-L, hydrogen-D, benzoyl, benzenesulfonyl, glutaryl, pyroglutamyl, carbobenzoxy, D-serine, or carbobenzoxy-serine;

$R_2$ is hydrogen, phenyl, a straight, branched or cyclic alkyl having 1 to 4 carbons, or propionic acid;

$R_3$ is hydrogen, straight or branched or cyclic alkyl having 1 to 4 carbons, 4-aminobutane, or 3-guanidylpropane;

$R_4$ is methyl, 4-aminobutane, or 3-guanidylpropane;

$R_5$ is a fluorogenic moiety, severable from said compound by a proteolytic enzyme and having different fluorescent property when severed from said compound than when forming part of said compound.

The enzymes, when reacting with the substrate, remove the fluorogenic group $R_5$ producing an increase in its fluorescence. The increase of the fluorescence is an indication of the activity of the enzyme present. Specific enzymes thusly detectable include plasmin, thrombin, the factors $X_a$, $XI_a$, & $XII_a$, kallikrein, trypsin, elastase, urokinase, and cathepsin $B_1$.

6 Claims, No Drawings

ANALYTICAL FLUOROGENIC SUBSTRATES FOR PROTEOLYTIC ENZYMES

BACKGROUND

Many proteolytic enzymes along with their cofactors and inhibitors play an important role in the proper functioning of the human body. These enzymes, which catalyze the cleavage of proteins, regulate many delicate and important biochemical processes. The clotting of blood represents a complex mechanism of regulated reactions. The essential process of blood coagulation is the proteolytic conversion of soluble fibrinogen into insoluble fibrin by the enzyme thrombin. Thrombin arises from its inactive precursor prothrombin through a series of proteolytic reactions involving protein, lipoprotein and inorganic ion cofactors. Inhibitors regulate blood clotting at various steps throughout the complex process.

The amounts of these enzymes contained in the body fluids lie within ranges considered "normal." However, the concentrations or activities of these enzymes, their cofactors or inhibitors, on occasion may either exceed or fall below their usual levels. Detecting the abnormal levels of these constituents of the body fluids assumes importance for, inter alia, the following two reasons.

Firstly, imbalance in the level of a particular enzyme, cofactor or inhibitor may directly and adversely affect the chemical reaction it regulates. Thus, in the case of blood clotting, thrombin promotes the formation of the clot. An insufficient level of thrombin results in inadequate blood clotting activity. Elevated thrombin can induce the formation of undesired clots with deleterious consequences. The reciprocal situation exists with antithrombin III levels, the inhibitor of thrombin. Elevated levels retard the clotting process while reduced levels may allow excessive clotting to occur. Plasmin, the primary protease of fibrinolysis, prevents the accumulation of fibrin clots. Excess levels, again, interfere with clotting while an insufficient level may permit the accumulation of undesired clots.

Secondly, such enzymes arise from biochemical reactions necessary for the maintenance of normal health. The concentration and activity of the enzymes is an indication as to the rate of these entire reactions themselves. Thus, detecting the levels of these enzymes can provide an indirect indication of an improper physical condition.

Several obstacles must be resolved before the detection of proteolytic enzymes can be used as a reliable diagnostic tool. Since these compounds exist in extremely small concentrations within the body fluids containing them, the usual chemical procedures are not sensitive enough to detect these enzymes.

An important advance in the quantitative determination of enzymes appears in U.S. Pat. No. 3,862,011 issued to R. E. Smith which discloses peptide derivatives of 4-methoxy-2-napthylamine. These compounds serve as substrates for proteolytic enzymes in tissue homogenates. The enzymes remove the 4-methoxy-2-napthylamine group from the peptide substrate. The cleaved group then reacts with a diazonium salt to form an azo dye. The intense color of the azo dye allows a spectrophotometric determination of concentration. The amount of the enzyme present is determined by comparison with a standard curve obtained by running similar tests with known enzyme concentrations.

U.S. Pat. No. 3,884,896 to G. E. B. Blomback et al. approaches the measurement of proteases in a manner similar to that described in the Smith patent. However, the Blomback et al. patent utilizes a chromophore, p-nitroaniline, attached to peptide molecules. The enzyme cleaves the chromophore which then undergoes direct spectrophotometric determination.

SUMMARY

Employing a fluorophore instead of a chromophore on a substrate molecule allows for the determination of smaller quantities of protease enzymes within body fluids. Attaching this fluorogenic group to particular peptide sequences further increases the sensitivity of the determination as well as enzyme specificity for the substrate.

Substrates incorporating these advantages may take the form of compounds responding to the formula:

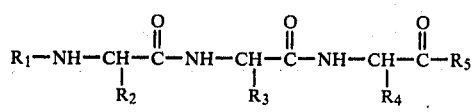

or acid salts thereof, wherein:

$R_1$ is hydrogen-L, hydrogen-D, benzoyl, benzenesulfonyl, glutaryl, pryroglutamyl, carbobenzoxy, D-serine or carbobenzoxy-serine;

$R_2$ is hydrogen, phenyl, a straight or branched or cyclic alkyl having 1 to 4 carbons, or propionic acid;

$R_3$ is hydrogen, straight or branched or cyclic alkyl having 1 to 4 carbons, 4-aminobutane, or 3-guanidylpropane;

$R_4$ is methyl, 4-aminobutane, or 3-guanidylpropane;

$R_5$ is a fluorogenic moiety, severable from said compound by a proteolytic enzyme and having enhanced fluorescence when severed from said compound than when forming part of said compound.

In particular, the fluorogenic group $R_5$ may take the form of either 4-methoxy-$\beta$-naphthylamine or 5-aminoisophthalic acid, dimethyl ester. Using the former has allowed the determination of as little as one unit of the factor $X_a$, 0.001 CTA unit of plasmin, and 0.005 NIH unit of thrombin using purified enzymes, spectrofluorometric measurements, and kinetic assay methods. The enzyme cleaves the fluorogenic group which then displays greater fluorescence when liberated than when attached to the substrate. Other enzymes which may be determined with fluorogenic substrate include factors $X_a$, $XI_a$, & $XII_a$, kallikrein, trypsin, elastase, urokinase, and cathepsin $B_1$. Carbobenzoxy represents a suitable amino protecting group. However, other protecting groups may also find use and can include benzoyl, benzenesulfonyl, glutaryl, or pyroglutamyl.

Activity of proteolytic enzymes is determined by mixing a solution of the enzyme with a substrate of the general formula given above. The solution, when subjected to light of a characteristic wavelength (excitation wavelength) absorbs some of the light energy emitting light at a longer wavelength, (emission wavelength). This emitted fluorescent light is used to determine the enzyme activity.

Each fluorophore has characteristic excitation and emission wavelengths. When using 4-methoxy-$\beta$-naphthylamine the optimum excitation and emission wavelengths in aqueous solutions at neutral pH are respectively 345 nm and 415 cm. The optimum wavelengths for 5-aminoisophthalic acid, dimethyl ester under the same conditions are 335 nm for excitation and 430 nm for emission.

DETAILED DESCRIPTION

The substrates given by the formula above may be used to determine the activity of various enzymes some of which are plasmin, thrombin, the factors $X_a$, $XI_a$, & $XII_a$, kallikrein trypsin, elastase, urokinse, and cathepsin $B_1$.

In discussing specific compounds, the following symbols stand for the groups indicated next to them:

| | |
|---|---|
| BZ = benozyl | gly = glycine |
| BZO$_2$ = benzenesulfonyl | glu = glutamic acid |
| GL = glutaryl | leu = leucine |
| PG = pyroglutamyl | lys = lysine |
| CBZ = carbobenzoxy | phe = phenylalanine |
| ala = alanine | pro = proline |
| arg = arginine | ser = serine |
| MNA = 4-methoxy-β-naphthylamine | val = valine |
| AIE = 5-aminoisophthalic acid, dimethyl ester | |

Specifically, plasmin reacts with the following compounds: H-D-val-leu-lys-MNA, H-D-phe-pro-arg-MNA, H-L-ala-ala-lys-MNA, BZ-phe-val-arg-MNA, BZ-glu-gly-arg-MNA, GL-ala-ala-lys-MNA, CBZ-gly-gly-arg-MNA, CBZ-phe-val-arg-MNA, CBZ-ala-ala-lys-MNA, CBZ-ala-lys-lys-MNA, CBZ-ala-arg-arg-MNA, H-D-val-leu-lys-AIE, H-D-phe-pro-arg-AIE, CBZ-phe-val-arg-AIE, and CBZ-ala-ala-lys-AIE.

Thrombin similarly reacts with a variety of compounds, including H-gly-pro-arg-MNA, H-D-phe-pro-arg-MNA, BZSO$_2$-phe-val-arg-MNA, BZ-phe-val-arg-MNA, BZ-gly-pro-arg-MNA, GL-phe-val-arg-MNA, GL-phe-gly-arg-MNA, GL-gly-pro-arg-MNA, PG-gly-pro-arg-MNA, CBZ-gly-gly-arg-MNA, CBZ-phe-val-arg-MNA, CBZ-phe-gly-arg-MNA, CBZ-gly-pro-arg-MNA, CBZ-ala-ala-lys-MNA, CBZ-ser-pro-phe-arg-MNA, H-D-phe-pro-arg-AIE, H-D-pro-phe-arg-AIE, GL-phe-gly-arg-AIE, CBZ-phe-gly- arg-AIE, CBZ-phe-val-arg-AIE, and CBZ-gly-pro-arg-AIE.

The factor $X_a$ can react with H-D-phe-pro-arg-MNA, BZ-glu-gly-arg-MNA, GL-phe-val-arg-MNA, GL-phe-gly-arg-MNA, CBZ-gly-gly-arg-MNA, and CBZ-gly-pro-arg-MNA.

Factors $XI_a$, $XII_a$, and kallikrein react with H-D-phe-pro-arg-AIE, H-D-pro-phe-arg-AIE, H-D-ser-pro-phe-arg-AIE, and CBZ-ser-pro-phe-arg-MNA.

Other proteases include trypsin which can react with CBZ-gly-gly-arg-MNA. Elastase will react with GL-ala-ala-ala-MNA. Urokinase has indicated reactivity with CBZ-gly-gly-arg-MNA and CBZ-ala-ala-lys-MNA. And, cathepsin $B_1$ has indicated reactivity with CBZ-ala-arg-arg-MNA.

Synthesis of (CH$_3$OOH) D-phe-pro-arg-(HCl) AIE

A suspension of 6 g (1.9×10$^{-2}$ molar) of CBZ-arg in 25 ml dimethylformamide (DMF) at −15° C. received 0.1 ml n-methylmorpholine and 2.6 ml (1.9×10$^{-2}$ molar) isobutyl chloroformate. After stirring at −15° C. for 45 minutes, this mixture received, in a dropwise fashion over a 10 minute period, a solution of 4 g (1.9×10$^{-2}$ molar) of 5-aminoisophthalic acid, dimethyl ester in 15 ml DMF. This latter mixture was stirred at −15° C. for 1 hour, 0° C. for 1 hour, and lastly overnight at ambient temperature. After the removal of the solvent under vacuum, the isolated oil was stirred in saturated sodium bicarbonate and then distilled water to yield a white solid. Seven grams of dry product resulted from this procedure.

Fifteen (15) ml ethanol and 0.5 ml acetic acid received 500 mg of the solid produced above. To this solution was added 150 mg of 10% palladium on charcoal (Pd/C). Hydrogen gas was then bubbled through this mixture for 16 hours. After filtration, the solvent was removed to yield 440 mg of material which gave a positive ninhydrin test and consisted of arg-AIE (HCl) acetate salt.

A solution of 442 mg (1.7×10$^{-3}$ molar) of CBZ-proline in 3 ml ethyl acetate and 150 ml n-methylmorpholine at −15°, received 275 mg (2.0×10$^{-3}$ molar) of isobutyl chloroformate. After eight minutes, this mixture then received a pre-cooled solution containing 694 mg (1.7×10$^{-3}$ molar) of the arg-AIE (HCl) acetate salt dissolved in 2 ml dimethylacetamide and 150 μl n-methylmorpholine. This mixture remained at −10° C. for 1 hour and then was stirred overnight at ambient temperature. The solvent was removed under vacuum and the resulting material chromatographed over silica gel, using CHCl$_3$/EtOH (7:3) as the eluent to yield 188 mg of product. The product was dissolved in ethyl alcohol and acetic acid to which was added Pd/C (10%). After bubbling hydrogn through it and filtration, removing the solvent yielded pro-arg-(HCl) AIE.

A solution of 260 mg (8.6×10$^{-4}$ molar) of CBZ-D-phenylalanine in 3 ml tetrahyrofuran (THF) and 142 μl of n-methylmorpholine received, at −15° C., 142 mg (1.0×10$^{-3}$ molar) of isobutyl chloroformate. To this latter mixture, after 8 minutes, was added a precooled solution of 8.6×10$^{-4}$ molar of the pro-arg-(HCl) AIE, produced above, in 3 ml dimethylacetamide and 142 μl n-methylmorpholine. This latter mixture remained at −10° C. for one-half hour and then at ambient temperature overnight. Evaporating the solvent under vacuum produced an oily material which was then chromatographed over silica gel using CHCl$_3$/ETOH (8:2) as the eluent. Removing the solvent left an oil.

This oil was dissolved in 3 ml ethyl alcohol which contained 6 drops of acetic acid. The solution additionally received 30 mg of Pd/C (10%) and had hydrogen bubbled through it for 2 hours. After filtration and evaporation of the solvent, 88 mg of the final product remained which gave a positive ninhydrin test.

Synthesis of glutaryl-phe-gly-arg (HCl) MNA

A solution of 170 mg (4.7×10$^{-4}$ molar) of CBZ-phe-gly in 2 ml THF received, at −10° C., equal molar amounts of n-methylmorpholine (50 mg) and isobutyl chloroformate (65 mg). After 5 minutes, this combination received a solution of 200 mg (4.7×10$^{-4}$ molar) of arg-MNA.2HCl and an equal molar amount of n-methylmorpholine in 13 ml DMF. The mixture was stirred at −5° C. for one hour and then at ambient temperature overnight. The resulting solution underwent filtration and removal of the solvent, with the residue chromatographed over silica gel. Evaporating the solvent yielded an oil which, when solidified, produced 200 mg of CBZ-phe-gly-arg (HCl) MNA.

A solution containing 75 mg of the above product in 2 ml methanol received 10 mg of 5% Pd/C. After bubbling hydrogen through the mixture for 5 hours, the catalyst was removed and the solvent evaporated. The resulting oil was dissolved in 1 ml methylene chloride and 0.3 ml DMF. The solution then received 15 mg glutaric anhydride. After standing overnight, no color developed upon subjecting the product to the ninhydrin test. This indicated the completion of the reaction. Adding ether to the mixture caused the formation of an oil. Trituration with chloroform caused the oil to solidify.

Fluorescent Substrate Assay for Plasminogen Utilizing D-val-leu-lys-AIE

Purified plasminogen, approximately 9.7 CTA units/ml in 50% glycerol, was obtained from National Institutes of Health, Bethesda, Maryland. It was diluted 1:2 in the assay buffer, 0.05 M Tris, 0.05 M glycine and 0.01% Brij-35, pH 8.0, and used as the reference plasminogen in the tests.

Streptokinase, 100,000 units/vial, obtained from Lederle Laboratories, Pearl River, N.Y., as Varidase was reconstituted in 10.0 ml 0.05 M Tris, 0.1 M glycine, pH 7.5, and stored at 20° C. Before use, the streptokinase was thawed and diluted to 2,000 units/ml in the same buffer.

TFA-D-val-leu-lys (TFA)-AIE, molecular weight 777.8, was obtained from Enzyme Systems Products, Inc., P.O. Box 1191, Indianapolis, Indiana. It was dissolved in the assay buffer to a concentration of 0.8 mM/liter and warmed to 37° C. before use. A $K_m$ value of $3.1 \times 10^{-4}$ M (37° C.) was determined within the assay system using the Lineweaver-Burk equation.

Blood specimens from laboratory workers with normal prothrombin and partial thromboplastin times were collected in plastic tubes containing one volume of 3.8% trisodium citrate for each nine volumes of blood. The specimens were centrifuged at 1,500 to 2,000 g for 10 to 15 minutes to obtain the plasmas which were then stored at $-20°$ C. and thawed prior to assay.

The assays were performed with 10 µl of plasma sample or diluted reference plasminogen added to 0.5 ml streptokinase solution. The reagents were vortex-mixed, incubated for 15 minutes at 37° C. to convert the plasminogen to its active for plasmin, and stored at 4° C. until assayed. From each of these activation mixtures 200 µml was transferred to a cuvet containing 2.0 ml of substrate solution pre-warmed to 37° C. The plasmin activity was determined by kinetic measurement of the released 5-aminoisophthalic acid dimethyl ester over a 2-4 minute interval, using a Model 430 spectrofluorometer from G. K. Turner Association, Palo Alto, Calif. The instrument was equipped with a controlled temperature sample cell holder and Model EV-200 recorder from Health Schlumberger, Benton Harbor, Mich. The excitation and emission wavelength and slit width settings were $335 \times 430$ nm and $60 \times 15$ nm respectively. The recorder chart speed was 1 inch/min. Disposable TPX plastic cuvets, $10 \times 8 \times 50$ nm, were used.

The plasmin activity of each sample expressed in CTA units/ml was calculated by comparison of the relative fluorescent rate of the sample with that of the reference plasminogen (4.85 CTA units/ml) as follows:

$$\text{Plasmin, CTA units/ml} = \frac{\text{Relative Rate of Sample}}{\text{Relative Rate of Reference Plasminogen}} \times 4.85$$

Plasma plasminogen values determined by this fluorescent substrate method were compared with the results from two reference methods. M-Partigen ™ Plasminogen Kits from Behring Diagnostics (American Hoechst Corporation, Somerville, N.J. 08876) were used to determine plasminogen concentration in mg/dl by the radial immunodiffusion technique. A standard caseinolytic assay method was used to measure the plasmin activity generated by streptokinase activation of each plasma sample. In the caseinolytic assay method, the relatively large sample volume required acid pre-treatment of the plasmas to destroy plasmin inhibitors prior to activation.

Good agreement was obtained between the fluorescent substrate assay and the two reference methods. The correlation coefficients obtained from least squares analyses of the data were 0.98 for the fluorescent versus caseinolytic assay, and 0.99 for the fluorescent versus radial immunodiffusion assay.

The precision of the fluorescent substrate assay for plasma plasminogen determinations was less than 5% for levels for plasminogen over the normal range.

Fluorescent Substrate Assay for Heparin Utilizing D-phe-pro-arg-AIE

Five normal blood specimens were collected daily in siliconized glass tubes containing 3.8% trisodium citrate for each 9 volumes of blood. The plasma was obtained by centrifugation of the blood at 1,240 g for 15 minutes. The resulting individual plasma samples were pooled and stored at 4° C. until used. Part of the plasma was diluted 1:40 in a general assay buffer for use in all the determinations, including the standard and test plasmas, as an equalizer of AT-III activity. The general assay buffer contained 0.25 M glycine in 0.03 M NaCl with 2 mM $K_2$EDTA and 0.01% trimerosal with the pH adjusted to 8.3 using 5 N NaOH.

Beef lung sodium heparin containing 10,000 U.S.P. units/ml was obtained from the Upjohn Company (Kalamazoo, Michigan 49001). The heparin underwent dilution to 80 units/ml with the general buffer given above. Heparin standards were prepared in the pooled plasma at concentrations of 0.1, 0.2, 0.4 and 0.8 units/ml.

The D-phe-pro-arg-AIE, diacetate, having a molecular weight of 728.8, was prepared in absolute ethanol at a concentration of 11.2 mg/ml and stored at 4° C. Before use, the stock solution was diluted in the general buffer to a concentration of 0.19 mM and warmed to 37° C. A $K_m$ value of $5.4 \times 10^{-5}$ M at 37° C. was determined within the assay system using the Lineweaver-Burk equation.

Lyophilized human thrombin containing 2,500 NIH units/mg were obtained from Calibiochem (San Diego, Calif. 92112). This material was dissolved to 10 units/ml with a buffer solution containing 0.05 M glycine, in 0.15 M NaCl having a pH of 5.0 with 2 mM $K_2$EDTA and 0.01% bovine serum albumin. The diluted solution was stored in aliquots at $-20°$ C. Before use, the thrombin was thawed and further diluted with the same solution to 2 NIH units/ml.

For this experiment, the Perkin Elmer spectrophotometer had an excitation wavelength setting of 335 nm with a slit width of 6 nm and the emission wavelength setting of 430 nm with a slit width of 12 nm. Volumes of 200 µl of 1:40 diluted normal plasma and 5 µl of test plasma or standard heparin in plasma were added to a sample cuvette and warmed to 37° C. Fifty (50) µl of thrombin having 0.1 NIH unit was added and the reagents mixed. After preincubation for 60 sec at 37° C., 2.0 ml of the substrate solution containing, 140 mg/l, pre-warmed to 37° C. was added, and the contents of the cuvette mixed by inversion. Uninhibited thrombin was determined by kinetic measurement of the released AIE over a 2 to 4 minute interval. Assay values were calculated according to the following equation with the blank result determined in the absence of heparin:

$$\% \text{ initial thrombin} = \frac{\text{test or standard result} \times 100}{\text{blank result}}$$

Table 2 gives the precision of standard heparin measurements determined according to the above procedure. The within and between-day precision for heparin standards at 0.1 to 0.4 units/ml was better than ±5%. The reported anticoagulant concentration range of heparin of 0.2 to 0.4 units/ml of plasma lies within the standard range.

| Assay Precision for Standard Heparin Determinations | | |
|---|---|---|
| Heparin, U.S.P. U/ml. | x̄, % Initial Thrombin | CV, % |
| Within-day, n = 4 | | |
| 0.1 | 93.4 | 1.5 |
| 0.2 | 83.0 | 3.6 |
| 0.4 | 61.3 | 4.4 |
| 0.8 | 28.0 | 10.0 |
| Day-to-day, n = 5 | | |
| 0.1 | 91.1 | 2.9 |
| 0.2 | 79.8 | 3.3 |
| 0.4 | 59.6 | 3.1 |
| 0.8 | 30.2 | 11.8 |

The reduced precision accompanying the measurements of the highest heparin standard, 0.8 units/ml, may result from assay timing errors. Experiments involving different incubation times showed a greater dependence of this heparin concentration upon this variable.

Increasing the preincubation time or reducing the thrombin concentration did, however, improve the assay's sensitivity. Freezing heparin standards prepared in plasma with a low platelet count of around 75,900/mm³ at −20° C. and subsequently thawing them at 22° to 28° C. produced some loss in the measured heparin activity.

These data are consistent with the work of others suggesting that plasma standards and test samples may require special treatment to reduce or eliminate platelets if the samples are to be stored frozen before assay.

Determinations were also made with WHO heparin preparations, bovine mucosal working reagent (no. 63/10) and porcine mucosal standard (Third International Standard no. 65/69). On the basis of their stated activities, there was good agreement between the dose response curves for these two preparations. The commercial beef lung heparin gave a standard curve which proved less sensitive and varied from the WHO standard curves by approximately 20%. These results may be related to the reported discrepancy between lung and mucosal heparin activities.

The sensitive detection of thrombin with the fluorescent substrate assay appears to allow its use rather than the factor $X_a$ for determining plasma heparin anticoagulant activity. Clotting interference is not encountered since only 1.10 NIH unit of thrombin and 10 μl of total plasma are employed in each determination. The assay precision of better than ±5% over the heparin anticoagulant range at least equalled or excelled the precision of the standard clotting assays designed for the measurement of heparin. The assay range would appear acceptable for routine monitoring of heparinized patient samples. However, increasing the preincubation time or reducing the amount of thrombin used can increase the assay sensitivity as required.

Accordingly, what is claimed is:

1. A method for determining plasmin or plasmin-like enzymes in a fluid comprising:

A. mixing said fluid with a fluorogenic substrate of the formula

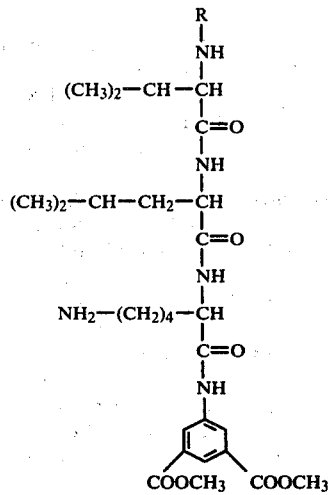

or acid salts thereof, wherein R is hydrogen-L, hydrogen-D, benzoyl, benzene sulfonyl, glutaryl, pyroglutamyl, carbobenzoxy, D-serine or carbobenzoxy-serine, thereby forming a substrate-containing fluid, whereby said substrate is enzymatically hydrolyzable by said plasmin, or plasmin-like enzymes to yield 5-aminoisophthalic acid dimethyl ester;

B. exposing said substrate-containing fluid to light of a wavelength suitable for causing fluorescent emission by said 5-aminoisophthalic acid dimethyl ester; and C. while exposing said substrate-containing fluid to said light, measuring the fluorescent emission of said fluid.

2. The method of claim 1 wherein R is hydrogen-D.

3. The method of claim 1 or 2 wherein said substrate-containing fluid is exposed to light of a wavelength of about 335 nanometers, and said fluorescent emission is measured at a wavelength of about 430 nanometers.

4. A method for determining thrombin, trypsin or thrombin or trypsin-like enzymes in a fluid comprising:

A. mixing said fluid with a fluorogenic substrate of the formula

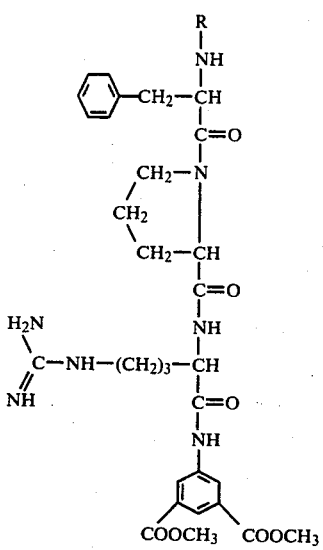

or acid salts thereof, wherein R is hydrogen-L, hydrogen-D benzoyl, benzene sulfonyl, glutaryl, pyroglutamyl, carbobenzoxy, D-serine or carbobenzoxy-serine, thereby forming a substrate-containing fluid, whereby said substrate is enzymatically hydrolyzable by said thrombin, trypsin, or thrombin or trypsin-like enzymes to yield 5-aminoisophthalic acid dimethyl ester;

B. exposing said substrate-containing fluid to light of a wavelength suitable for causing fluorescent emission by said 5-aminoisophthalic acid dimethyl ester; and C. while exposing said substrate-containing fluid to said light, measuring the fluorescent emission of said fluid.

5. The method of claim 4 wherein R is hydrogen-D.

6. The method of claim 4 or 5 wherein said substrate-containing fluid is exposed to light of a wavelength of about 335 nanometers and said fluorescent emission is measured at a wavelength of about 430 nanometers.

* * * * *